United States Patent
Cady et al.

(10) Patent No.: US 6,416,472 B1
(45) Date of Patent: Jul. 9, 2002

(54) METHOD AND DEVICE FOR MEASURING COGNITIVE EFFICIENCY

(75) Inventors: Roger K. Cady; Kathleen U. Farmer, both of Ozark, MO (US)

(73) Assignee: Edus Inc., Springfield, MO (US)

( * ) Notice: Subject to any disclaimer, the term of this patent is extended or adjusted under 35 U.S.C. 154(b) by 0 days.

(21) Appl. No.: 09/571,990

(22) Filed: May 16, 2000

Related U.S. Application Data

(63) Continuation-in-part of application No. 09/185,310, filed on Nov. 3, 1998, now Pat. No. 6,066,092.
(60) Provisional application No. 60/064,879, filed on Nov. 6, 1997.

(51) Int. Cl.[7] .............................. A61B 5/00; A61B 5/04
(52) U.S. Cl. ...................... 600/300; 600/544; 128/920
(58) Field of Search ................................ 600/300, 301, 600/544, 545; 128/897, 898, 920, 921, 922, 923, 924, 925

(56) References Cited

U.S. PATENT DOCUMENTS

| | | | |
|---|---|---|---|
| 3,901,215 A | * 8/1975 | John ........................ | 600/544 |
| 4,816,470 A | 3/1989 | Dowle et al. | |
| 4,969,096 A | * 11/1990 | Rosen et al. ........... | 364/413.02 |
| 5,037,845 A | 8/1991 | Oxford | |
| 5,840,018 A | 11/1998 | Michaeli | |
| 5,911,581 A | * 6/1999 | Reynolds et la. ........... | 434/236 |
| 6,241,686 B1 | * 6/2001 | Balkin et al. ............... | 600/544 |

FOREIGN PATENT DOCUMENTS

| | | |
|---|---|---|
| FR | 2 522 175 | 8/1983 |
| FR | 2 672 201 | 8/1992 |

OTHER PUBLICATIONS

J.N. Blau, Migraine: Clinical, therapeutic, conceptual and research aspects, London, Chapman and Hall, 1987, pp. 4–7.
Roger K. Cady, Treating the Headache Patient, Ch. 6, New York, Marcel Dekker, Inc., 1995, pp. 101–118 and 121–122.
D. Reeves, et al., ANAM v3.11a/96 User's Manual, 1996 Update 1997, pp. 1, 10–14, 16–28, 32–35.
IMITREX Tablets leaflet, Feb. 1997.
Migraine Today, Migraine Information Center.
Cady, R.K.: "Diagnosis of Headache" Treating the Headache Patient, Ch. 6, Marcel Dekker, Inc., 1995, pp. 101–122, New York, XP000933674.
J.N. Blau, "Migraine: clinical, therapeutic, conceptual and research aspects," pp. 4–7, 1987, Chapman and Hall, London, XP 000933853.

\* cited by examiner

*Primary Examiner*—Kevin Shaver
*Assistant Examiner*—Navin Natnithithadha
(74) *Attorney, Agent, or Firm*—Husch & Eppenberger, LLC; Robert E. Muir; H. Frederick Rusche

(57) ABSTRACT

A method for measuring cognitive efficiency uses the following cognitive tests: Simple Reaction Time; Running Memory Continuous Performance Task; Matching to Sample; and Mathematical Processing Task. A device for measuring cognitive efficiency includes a microprocessor having a memory; the aforementioned cognitive tests loaded into the memory; a baseline stored in the memory, means for computing the score on a run of these tests and for storing the score in the memory; the means for computing being operative for comparing the score to the stored baseline; and means for indicating a cognitive change from the baseline. Changes in cognitive efficiency may be measured by comparing the results of the cognitive tests to a baseline.

21 Claims, 4 Drawing Sheets

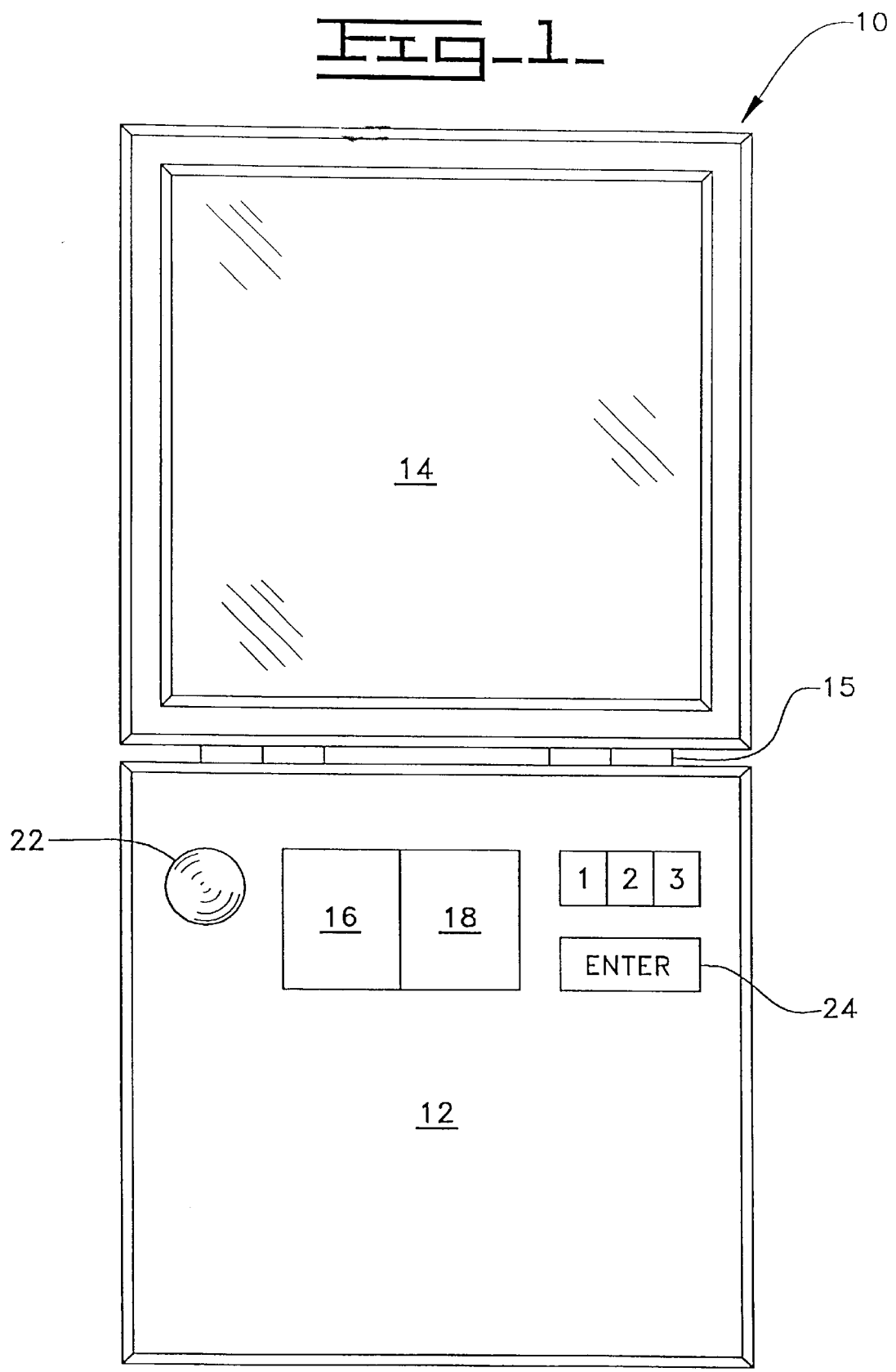

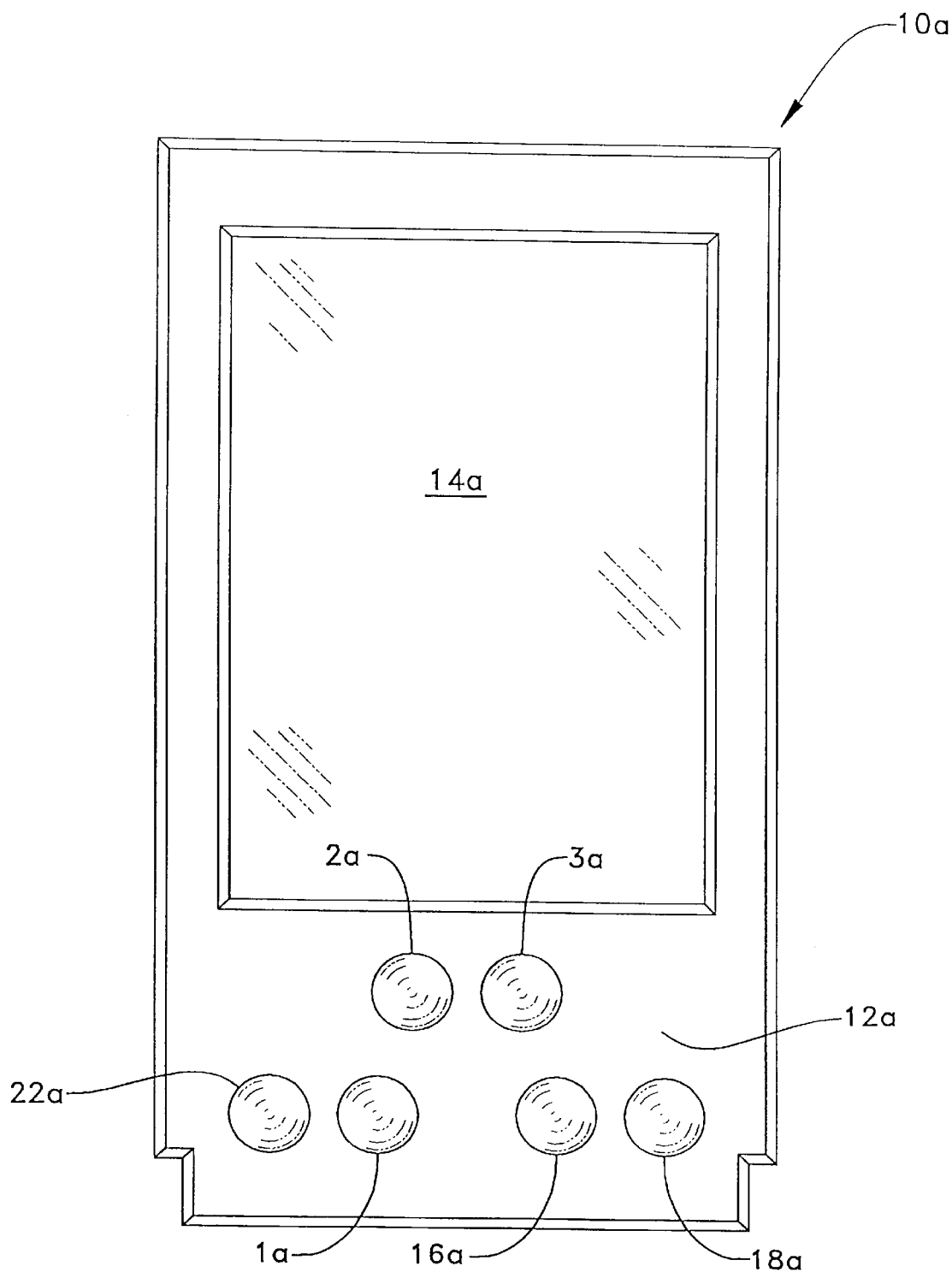

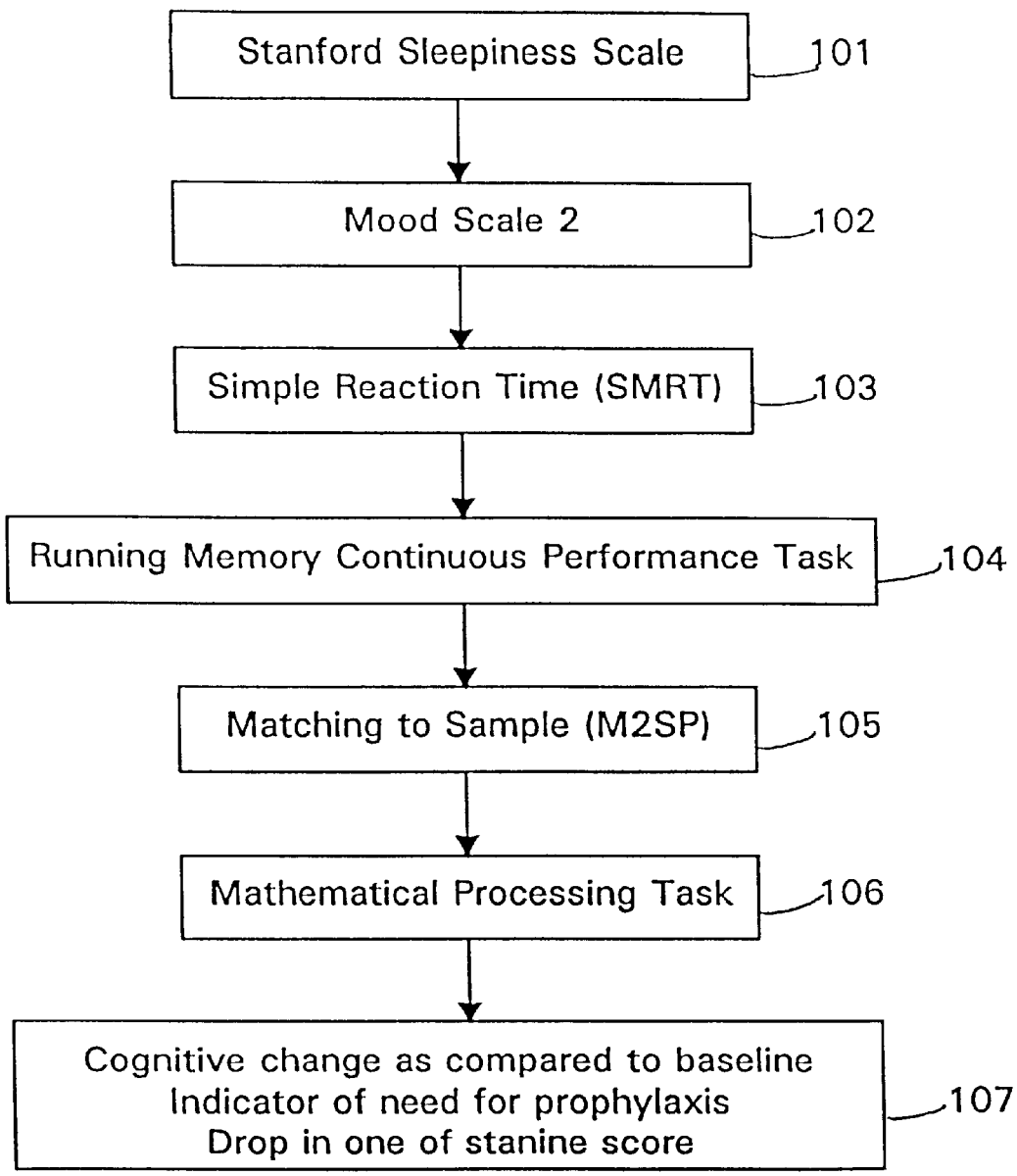
Fig_2

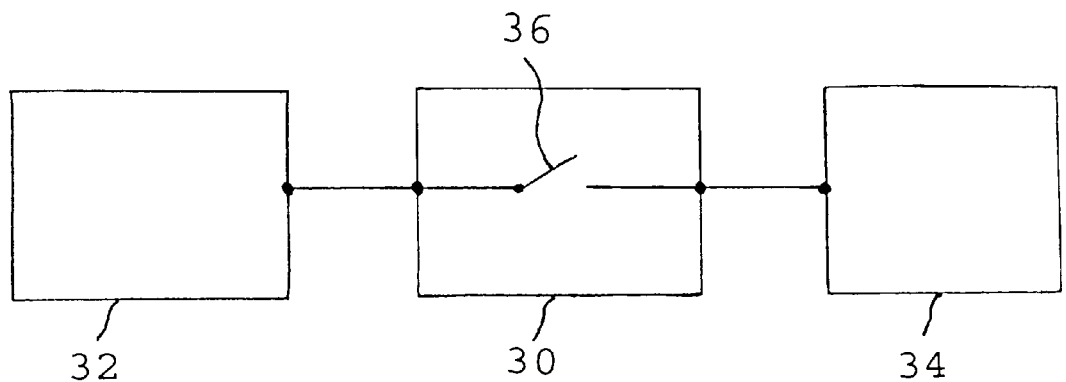
FIG_3A_
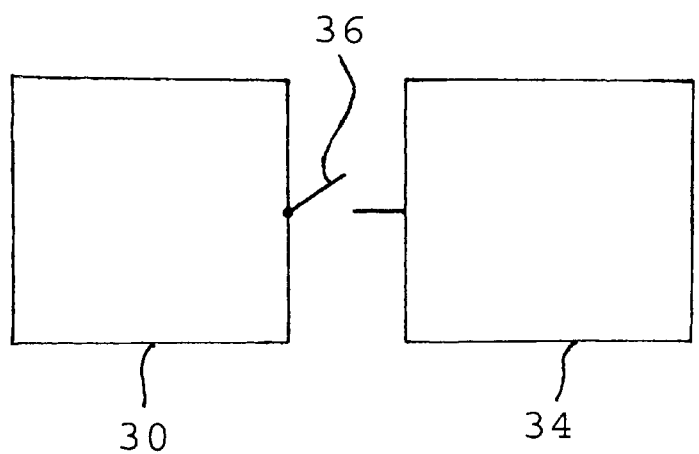
FIG_3B_

METHOD AND DEVICE FOR MEASURING COGNITIVE EFFICIENCY

CROSS REFERENCES

This application is a continuation-in-part of U.S. application Ser. No. 09/185,310, filed Nov. 3, 1998 now U.S. Pat. No. 6,066,092 which claims benefit of Provisional No. 60/064,879 filed Nov. 6, 1997.

FIELD OF THE INVENTION

The present invention relates generally to the medical field and, more particularly, to a method and device for measuring cognitive efficiency in humans.

BACKGROUND OF THE INVENTION

The measurement of cognitive efficiency has been limited to testing of a subjective nature, and results of such testing have not been available in real-time. In addition, current testing methods are limited in their ability to detect positive and negative changes in the cognitive efficiency of a test subject. It would be desirable to develop a method of measuring the level of cognitive efficiency and subsequent changes in cognitive efficiency by means of a purely objective test that yields results in real-time. Such a test should take into consideration reaction time, memory, spatial relationships, and mathematical integration.

The Automated Neuropsychological Assessment Metrics (ANAM) is a set of standardized batteries of cognitive tests, modified by neuropsychologists in the U.S. Armed Forces for precise measurement of cognitive processing efficiency of military personnel. The tests assess sustained concentration and attention, mental flexibility, spatial processing, cognitive processing efficiency, mood, arousal/fatigue level, and short-term, long-term and working memory. The ANAM is now in the public domain. The most recent version is ANAM V3.11a/96 which includes the following battery of tests:

1. Subject Demographics Form
2. Stanford Sleepiness or Sleep/Fatigue Scale
3. Mood Scale 2
4. Simple and Two-Choice Reaction Time
5. Sternberg Memory Search Tasks
6. Running Memory Continuous Performance Task
7. Mathematical Processing Task
8. Digit Set Comparison Task
9. Logical Reasoning-Symbolic
10. Tower of Hanoi (Tower Puzzle)
11. Stroop Color/Word Interference
12. Code Substitution (Letter/Symbol Comparison)
13. Code Substitution (Immediate and Delayed Recall)
14. Spatial Processing Task (Simultaneous)
15. Matching to Sample
16. Tapping (Left and Right Index Finger)
17. Modified Orientation and Amnesia Test It would be desirable to be able to use a subset of these tests to measure the cognitive efficiency of a human.

SUMMARY OF THE INVENTION

The present invention provides a method for measuring the cognitive efficiency in a human using the following cognitive tests: Simple Reaction Time; Running Memory Continuous Performance Task; Matching to Sample; Mathematical Processing Task. Change in cognitive efficiency may be measured by comparing the results of the cognitive tests to a baseline. Preferably the tests are administered in the listed sequence. Advantageously the tests are preceded by the Stanford Sleepiness Scale and Mood Scale 2 tests.

In a preferred arrangement there is provided a cognitive efficiency measurement device including a microprocessor having a memory, a battery of tests loaded into the memory of the microprocessor and including a Simple Reaction Time, a Running Memory Continuous Performance Task, a Matching to Sample, and a Mathematical Processing Task; a baseline stored in memory; means for computing the score on a run of the tests; the means for computing being perative for comparing the score to the stored baseline; and means for indicating a cognitive change.

These and other objects, aspects, features and advantages of the present invention will become apparent from the following detailed description when taken in conjunction with the referenced drawings.

BRIEF DESCRIPTION OF THE DRAWINGS

Reference is now made more particularly to the drawings which illustrate the best presently known mode of carrying out the invention and wherein similar reference characters indicate the same parts throughout the views.

The accompanying drawings illustrate two devices and one method for carrying out the present invention and wherein:

FIG. 1 is a plan view of a hand-held computer which is one apparatus for determining cognitive change in a human;

FIG. 1A is a plan view of a palm-top type computer which is another apparatus for determining cognitive change in a human;

FIG. 2 is a flow chart illustrating the steps and sequence of a method for measuring cognitive efficiency and change in cognitive efficiency in humans;

FIG. 3A is a schematic view of an apparatus to control the operation of a machine with a starting mechanism;

FIG. 3B is a schematic view of an apparatus to control the operation of a machine without a starting mechanism.

DETAILED DESCRIPTION

FIG. 1 shows a cognitive efficiency measurement device in the form of a hand-held computer, generally designated 10, and having a key pad 12 and a screen 14 which advantageously is at least four inches (10.16 cm.) square. A hinge 15 is provided so the screen 14 may be conveniently folded down upon the key pad 12 for storage or transporting. When open the computer 10 is conveniently about 5"×9" (12.7 cm. by 22.86 cm.) in size. The key pad 12 has a built-in set of two mouse buttons 16,18, a start/stop or on/off button 22, an enter key 24, and Mood Scale 2 keys 1, 2 and 3. As used herein the terms "buttons" and "keys" are intended to mean the same thing. The computer 10 contains memory chips (not shown) which have a set of programmed cognitive tests 103–106 (hereafter described) and which record a person's performance time in milliseconds on those tests. An objective standard may be directly entered and stored in the memory chips as a baseline, or a score from a prior battery of tests, converted to stanine, may be used as the baseline. Subsequent trials are similarly scored, converted to stanine, and compared to the baseline.

FIG. 1A shows a palm-top type computer 10*a* which, when programmed with the cognitive tests 103–106, performs the same functions as hand-held computer 10.

Accordingly, the same functional parts identified in FIG. 1, are identified in FIG. 1A with the same numerals and the letter "a". Further description is deemed unnecessary. It is believed that the largest palm-top computer now available is 7.8 inches (19.81 cm.) long and the screen 14a is not as large as the desired four inches (10.16 cm.) square. However, this deficiency is offset by the savings in using mass produced devices.

FIG. 2 shows the sequence of a cognitive efficiency measurement method. From the seventeen tests of the original ANAM, four subtests were selected and sequenced for measuring cognitive processing efficiency, as follows:

1. Simple Reaction Time (SMRT), 103
2. Running Memory Continuous Performance Task (CPT), 104
3. Matching to Sample (M2SP), 105
4. Mathematical Processing Task (MATH), 106

Also included are two preliminary measures of alertness and mood that are also part of the ANAM:

1. Stanford Sleepiness Scale, 101
2. Mood Scale 2, 102.

Description of Subtests

1. The first step 101 is Stanford Sleepiness Scale which consists of seven statements that describe the present state of alertness or sleepiness and are numbered from one to seven, with one being highly alert and seven being close to sleep. Individuals rate their level of alertness prior to taking the first subtest of the battery. It provides a way to monitor fatigue over the course of repeated measures. Subjective ratings may be correlated with measured performance.
2. The second step 102 is Mood Scale 2 which consists of a list of thirty-six adjectives that are rated on a three-point scale. Using mouse button 16 participants respond to each adjective by indicating "yes," "moderately," or "no," based on how they feel at the present time. The Mood Scale 2 categories include anger, happiness, fear (anxiety), depression, activity, and fatigue.
3. The third step 103 is Simple Reaction Time (SMRT) which presents a simple stimulus on the screen (*). In response, the individual presses the mouse button 16 each time the stimulus appears. The Reaction Time measures the speed of the motor response, the peripheral nerve conduction velocity. This represents the "hardware" of the nervous system in terms of input, followed by motor response. Actual cognitive processing time is not involved in this test.
4. The fourth step 104 is Running Memory Continuous Performance Test (CPT) which is a continuous letter comparison task. A randomized sequence of upper-case letters, A through Z, is presented one at a time in the center of the computer screen 14. The person presses button 16 if the letter on the screen matches the letter that immediately preceded it; and different button 18 if the letter on the screen is different than the immediately preceding letter. The task lasts approximately five minutes. The CPT was specifically designed to assess components of memory, attention, efficiency and consistency. This task is forced paced, with individuals having only a brief time in which to respond.
5. The fifth step 105 is Matching to Sample (M2SP) and consists of a number of trials that begins with a first design being presented in the center of the screen 14 for three seconds, followed by a showing that contains two designs. The person matches one of the two designs with the first design or sample by pressing the appropriate button 16 or 18. The design is a 4×4 checkerboard and varies by the number of cells that are shaded from one cell through twelve cells.
6. The sixth step 106 is Mathematical Processing (MATH) and involves arithmetic problems presented in the middle of the screen 14. Working from left to right, the person solves the addition and subtraction and decides if the answer is greater or less than the number 5.

As indicated, the scores are recorded in the memory of the computer 10 and the score on the third trial of these sequenced cognitive tests 103–106 is used as a baseline. As indicated above, a standardized baseline may also be stored in the computer memory. Subsequent trials measure cognitive change as compared to the baseline. An objective standard score or scores received by other tested humans may be directly entered into and stored in the computer as the baseline if it is desired to compare the cognitive efficiency of a human to an objective standard or to other humans.

It will be appreciated by those in the art that the above described tests are purely objective and examine four key areas of cognitive function: reaction time, memory, spatial relationships, and mathematical integration. In addition, the method provides results from these tests almost immediately. The method also allows for the detection of positive or negative change in cognitive efficiency of a test subject by comparing the most recent test results to an established baseline cognitive efficiency measurement for the test subject.

The method of measuring cognitive efficiency has practical applications as both a testing means and a security apparatus. The method can be used to determine the effects of new pharmaceuticals on humans prior to their distribution. For instance, trials by pharmaceutical companies or the Food and Drug Administration could determine whether a new drug induces drowsiness in or otherwise impairs a user of the medication by comparing measurements taken after administration of the medication with a baseline.

The method can also be incorporated into an apparatus arranged to prevent an operator from using motive or stationary machinery, such as an automobile, truck, tractor, airplane, watercraft, power tool, or industrial equipment, while in a fatigued condition or under the influence of alcohol or drugs. As an example, a cognitive efficiency measurement device can be connected between a power source and a work device. In one embodiment shown in FIG. 3A, a connection of the cognitive efficiency measurement device 30 with a starting mechanism 32, such as an ignition circuit or power switch, and an engine 34 or other motive force of a machine is in the form of a switch 36 that, when open, breaks the connection between the starting mechanism 32 and the engine 34, thereby preventing starting of the engine 34. The switch 36 can be moved to the closed position, thereby reconnecting the starting mechanism 32 and the engine 34 and allowing the engine 34 to be started, only when the cognitive efficiency device 30 sends a signal to the switch 36. In this arrangement, the starting mechanism 32 is allowed to initiate operation of the machine when the switch 36 is in the closed position. In another arrangement shown in FIG. 3B, the cognitive efficiency device 30 acts as the starting mechanism. Therefore, the operation of the machine is immediately initiated when the switch 36 moves to the closed position. The device 30 would send the signal only when the operator activates the cognitive efficiency device 30 and receives a satisfactory score on the cognitive tests. A satisfactory score would be defined as a score that equals or surpasses a standard baseline entered directly into the device or the operator's personal baseline measurement.

Other objects, features and advantages of the present invention will be apparent to those skilled in the art. While preferred steps of the method have been illustrated and described, this had been by way of illustration and the invention should not be limited except as required by the scope of the appended claims.

We claim:

1. A method of measuring cognitive efficiency in a human including performing only four cognitive tests including a Simple Reaction Time test, a Running Memory Continuous Performance test, a Matching to Sample test, and a Mathematical Processing test.

2. A method of measuring cognitive efficiency in a human as set forth in claim 1, wherein the cognitive tests are performed in the order listed.

3. A method of measuring cognitive efficiency in a human as set forth in claim 1, wherein the cognitive tests are preceded by the steps of performing a Stanford Sleepiness Scale test and a Mood Scale 2 test.

4. A method of measuring cognitive efficiency in a human as set forth in claim 1, including the steps of administering and scoring the cognitive tests by a computer, and storing the scores received on the cognitive tests in the computer.

5. A method of measuring change in cognitive efficiency in a human including:
performing only four cognitive tests; and, comparing scores received on the cognitive tests to a baseline.

6. A method of measuring change in cognitive efficiency in a human as set forth in claim 5, wherein the step of performing cognitive tests include performing a Simple Reaction Time test, a Running Memory Continuous Performance test, a Matching to Sample test, and a Mathematical Processing test.

7. A method of measuring change in cognitive efficiency in a human as set forth in claim 6, wherein the cognitive tests are performed in the order listed.

8. A method of measuring change in cognitive efficiency in a human as set forth in claim 6, wherein the steps of performing cognitive tests are preceded by the steps of performing a Stanford Sleepiness Scale test and a Mood Scale 2 test.

9. A method of measuring change in cognitive efficiency in a human as set forth in claim 5, including the steps of administering and scoring the cognitive tests by a computer, and storing the scores received on the cognitive tests in the computer.

10. A device for measuring change in cognitive efficiency in a human including a microprocessor having a memory, a battery of only four cognitive tests loaded into the memory of the microprocessor and including a Simple Reaction Time, a Running Memory Continuous Performance Task, a Matching to Sample, and a Mathematical Processing Task; a baseline stored in the memory of the microprocessor, means for computing a score on a run of the tests and for storing the score in the memory; the means for computing being operative for comparing the score to the stored baseline; and means for indicating a cognitive change from the baseline.

11. A device for measuring change in cognitive efficiency in a human as set forth in claim 10, wherein the means for computing includes changing the score to stanine.

12. A device for measuring change in cognitive efficiency in a human as set forth in claim 11, wherein the means for indicating a cognitive change is operative upon a drop of one in stanine score as compared to the baseline.

13. A device for measuring change in cognitive efficiency in a human as set forth in claim 10, including a screen which is about 10 cm. square.

14. A device for measuring change in cognitive efficiency in a human as set forth in claim 10, including a screen and a key pad adjacent the screen.

15. A device for measuring change in cognitive efficiency in a human as set forth in claim 14, including means for hinging the screen and key pad so that they may be folded upon each other.

16. A device for measuring change in cognitive efficiency in a human as set forth in claim 14, wherein the key pad includes a plurality of mouse buttons.

17. A device for measuring change in cognitive efficiency in a human as set forth in claim 14, wherein the key pad includes a plurality of Mood Scale 2 buttons.

18. A device for measuring change in cognitive efficiency in a human as set forth in claim 14, wherein the key pad includes an on/off button, two mouse buttons, and three Mood Scale 2 buttons.

19. A device to control the initiation of operation of a machine, including:
a cognitive efficiency measurement device connected with the machine, the device including a microprocessor having a memory, a battery of only four cognitive tests loaded into the memory of the microprocessor and including a Simple Reaction Time, a Running Memory Continuous Performance Task, a Matching to Sample, and a Mathematical Processing Task; a baseline stored in the memory, means for computing a score on a run of these tests and for storing the score in the memory; and the means for computing being operative for comparing the score to the stored baseline and for sending a signal when the score equals or surpasses the stored baseline;
a switch having first and second positions and connecting the cognitive efficiency measurement device and the machine, the switch being movable to the second position when the signal is received from the cognitive efficiency measurement device for operation of the machine.

20. A device to control the initiation of operation of a machine according to claim 19, so constructed and arranged that when the switch is in the second position the operation of the machine is immediately initiated.

21. A device to control the initiation of operation of a machine according to claim 19, including a starting mechanism that may be activated to initiate operation of the machine when the switch is in the second position.

* * * * *